United States Patent [19]

Orr, Jr. et al.

[11] Patent Number: 4,920,810
[45] Date of Patent: May 1, 1990

[54] SAMPLE WARMING DEVICE FOR SURFACE AREA ANALYZER

[75] Inventors: Cyde Orr, Jr., Dunnwoody; Ronnie W. Camp, Duluth, both of Ga.

[73] Assignee: Micromeritics Instrument Corporation, Norcross, Ga.

[21] Appl. No.: 157,880

[22] Filed: Feb. 19, 1988

[51] Int. Cl.$^5$ ............................................. G01N 15/08
[52] U.S. Cl. .................................................... 73/865.5
[58] Field of Search ................................ 73/865.5, 38

[56] References Cited

U.S. PATENT DOCUMENTS

| | | | |
|---|---|---|---|
| 2,788,657 | 4/1957 | Innes | 73/38 |
| 2,960,870 | 11/1960 | Nelsen | 73/865.5 |
| 3,211,006 | 10/1965 | Haley | 73/865.5 |
| 3,211,007 | 10/1965 | Atkins | 73/865.5 |
| 3,262,319 | 7/1966 | Orr Jr. | 73/865.5 |
| 3,464,273 | 9/1969 | Hendrix | 73/865.5 |
| 3,555,912 | 1/1971 | Lowell | 73/865.5 |
| 3,707,870 | 1/1973 | Herve | 73/38 |
| 3,771,367 | 11/1973 | Lowell | 73/865.5 |
| 3,783,697 | 1/1974 | Lowell | 73/865.5 |
| 3,850,040 | 11/1974 | Orr Jr. | 73/865.5 |
| 3,884,083 | 5/1975 | Lowell | 73/865.5 |
| 4,335,610 | 6/1982 | Scott | 73/865.5 |
| 4,489,593 | 12/1984 | Pieters et al. | 73/38 |
| 4,566,326 | 1/1986 | Lowell | 73/865.5 |

OTHER PUBLICATIONS

J.E. Stone and L.F. Nickerson, "A dynamic Nitrogen Adsorption Method for Surface Area Measurements of Paper", presented at the Annual Meeting of the Technical Section, Canadian Pulp & Paper Assoc., Montreal, Jan. 22–25, 1963.
Beta Scientific Corporation. "Proposal for an Automatic Surface Area Analyzer".
Aminco Sor-Bet Surface Area Analyzer Information Sheet, Copyright 1967.
Ettre, L.S., "Application of the Continuous Flow Method and the Model 212-D Sorptometer for Surface Studies", Perkin-Elmer.
Leeds & Northrup, "Automatic Surface Area Analyzer".
Quantachrome Corporation, "Monosorb Manual".
Micromeritics, "Instruction Manual for the Flosorb II 2300", (15 Apr. 1985).
Daeschner and Stross, "An Efficient, Dynamic Method for Surface Area Determinations", Analytical Chemistry, vol. 34, No. 9, Aug. 1962, p. 1150.

Primary Examiner—John Chapman
Assistant Examiner—Joseph W. Roskos
Attorney, Agent, or Firm—Jones, Askew & Lunsford

[57] ABSTRACT

An automated device for warming and cooling a sample is disclosed, and is particularly useful in connection with a flowing gas surface area analyzer. The device is capable of directing a flow of room temperature air onto a sample chamber after the chamber is removed from a coolant, thus rapidly warming the sample up to, but not exceeding, room temperature. In the disclosed embodiment, a Dewar flask containing coolant is mounted on an elevator platform. The flask is mechanically raised or lowered so as to immerse the sample chamber, located above the flask, in the coolant. A fan directs a flow of air onto the sample after the flask is lowered away from the sample chamber. A logic controller, connected to a timer, operates and regulates the cooling and warming process. The elevator assembly, fan and controller are disposed within a housing. The sample chamber is connected to gas input and output tubes, which are monitored by a detector for the composition of gas passing through the tubes. A method is also disclosed for analyzing the surface area of a sample using the device.

16 Claims, 4 Drawing Sheets

SAMPLE WARMING DEVICE FOR SURFACE AREA ANALYZER

TECHNICAL FIELD

The present invention relates to the measuring of surface area and extent of porosity in powdered and granular solid materials, and more particularly to an apparatus and method for measuring the low temperature adsorption of a gas onto a material and the subsequent desorption of the gas upon return to room temperature.

BACKGROUND ART

In carrying out chemical reactions and processes, it is important to know the surface area and pore volume of the catalytic materials employed, as these factors are related to the rate of reaction. As recognized in U.S. Pat. No. 2,788,657, issued to Innes Apr. 16, 1957, which is incorporated by reference herein, the catalytic reaction takes place on the surface of the catalytic material. Pore volume or structure is important, since it governs the diffusion of reactants and products to and from the surface of the catalytic material as well as exerting considerable influence upon the stability or life of the material.

One popular method for measuring the surface area and extent of porosity in powdered and granular solid materials involves the low temperature adsorption of an active gas from a mixture of an active and an inactive gas continuously flowing over a sample of the material. Nitrogen is most frequently the active gas and helium the inactive one. A typical mixture composition is 30% nitrogen and 70% helium. The use of nitrogen has been generally accepted as a standard method for determining surface area because of the close checks that could be obtained by such measurements where the area was known geometrically. Also, nitrogen is used because of its low cost, inertness and nonflammability.

In this method use is made of the phenomenon of adsorption of gas onto the surface of a solid at low (liquid nitrogen) temperatures. Gas sorption techniques utilize a theoretical model wherein the surface of the solid being measured is viewed as being covered by a monolayer of closely packed molecules of an adsorbed gas. If one can determine the amount of gas in the monolayer, the area covered by the monolayer can then be calculated from the product of the number of molecules in the monolayer multiplied by the cross sectional area of each molecule. See generally, U.S. Pat. No. 4,489,593 issued to Pieters, et al., Dec. 25, 1984, which is incorporated by reference herein.

In carrying out the conventional method the sample is initially heated to 150° to 200° C. with the mixed gas flowing about it to drive off gas and vapors picked up during exposure to the atmosphere and then cooled to room temperature and physically shifted to another position for analysis. The mixed gas flow is continued at the new location, but the sample temperature must be reduced to the temperature of liquid nitrogen to bring about adequate adsorption of nitrogen gas from the gas stream. This is generally accomplished by arranging the sample in a holder with inlet and outlet tubes extending upward so that a Dewar flask containing liquid nitrogen can be brought upward to immerse the sample and the lower portions of the tubes. Adsorption equilibration usually requires about 3 to 12 minutes for establishment.

Initially, the amount of $N_2$ passing through the detector per unit of time is considered to be the baseline equilibrium level, arbitrarily set at zero. When the sample material is cooled to liquid nitrogen temperature, $N_2$ is adsorbed onto the sample surface, causing a reduction in the amount of $N_2$ detected downstream. This $N_2$ drop continues until the adsorption of $N_2$ forms a monolayer on the sample. Then the $N_2$ level returns to the baseline equilibrium level, providing an indication that adsorption is complete.

When the sample is brought back up to room temperature, $N_2$ gas is desorbed from the sample surface, causing an increase in $N_2$ detected downstream. This increase continues until complete desorption has occurred. Then the $N_2$ level returns to the baseline equilibrium level. The measurements are integrated and the surface area of the sample calculated from the amount of $N_2$ adsorbed. During the measurement process, because of the physical conditions defined by the reaction equations, the pressure, volume and temperature of the $N_2$ measured downstream from the sample should remain stable. This stability provides the basis for a useful comparison between calibration measurements and sample run measurements.

The adsorbed nitrogen is desorbed by warming the sample to room temperature by any of several known techniques. The simplest way is to wait for the sample to warm naturally by being in the ambient atmosphere, as suggested by U.S. Pat. No. 3,884,083 issued to Lowell May 20, 1975. Unfortunately, warming by this method is slow. Some analyzers require the sample to be brought to room temperature within about 30 seconds, otherwise the gas flow disturbance created by the temperature change will erroneously register as a gas quantity and distort results. U.S. Pat. No. 3,884,083 also suggests that, when using butane as an adsorbate, a heating mantle can be employed to warm the sample. The temperature of the sample is not easily regulated and overheating is quite possible.

U.S. Pat. No. 4,489,593 discloses an apparatus which has a temperature controlled box which performs several functions, including: (1) heating an incoming gas line; (2) compensating for the temperature sensitivity of the electronic circuitry; (3) ensuring that the temperature in the gas line is constant; and (4) eliminating the effect of changes in ambient temperature on the gas. Since the gas passes through the box before entering the sample holder, it appears that the heated gas would raise the sample temperature to above room temperature when coolant is removed. The thermistor measures the temperature of the air in the box, and not the temperature of the sample holder; control of the temperature of one component does not necessarily control the temperature accurately of both components.

Another method is to blow heated air over the sample chamber. This does not work well because of the lack of control of the temperature at the desired target of room temperature. Unless the temperature of the sample itself is monitored closely, the target temperature can be exceeded, which can cause inaccuracies in the data obtained. Also, the sample cell rapidly frosts over from atmospheric water vapor once removed from the coolant and this white frost reflects much of the thermal radiation, thereby showing the time of warming and making it difficult to know precisely when to stop warming the sample chamber.

U.S. Pat. No. 2,788,657, which is incorporated by reference herein, replaces the liquid nitrogen bath after cooling with a water bath at room temperature. This method requires the manual manipulation of a second container by the user. There is a need then, for a convenient, automated means for controllably bringing a cooled sample to room temperature, without exceeding room temperature. There currently does not exist a means which rapidly and controllably raises the sample temperature for desorption. Such a means should be integrated into an automated analyzer system and should not increase the amount of time or attention required by a user.

SUMMARY OF THE INVENTION

The present invention solves the problems described above by providing an automated means for rapidly bringing a cooled sample to room temperature without exceeding room temperature, while requiring no additional user time or manipulation. The invention generally provides for directing a flow of room temperature air onto the sample, whereby the sample is warmed to room temperature in a controlled manner. The means for generating the flow of room temperature air, such as a fan, is activated after adsorption of gas is complete.

The present invention generally provides a flowing gas surface analyzer comprising a sample chamber for containing a sample of material to be analyzed; a means for flowing a stream of gas through the sample chamber containing the sample; a detector means for receiving the stream of gas downstream from the sample chamber and for providing a signal correlative with adsorption or desorption of the gas by the sample; a means for cooling the sample to a temperature at which adsorption of the gas by the sample occurs; a means for warming the sample comprising a means for directing a flow of room temperature air over the sample chamber such that the sample is warmed to a temperature at which desorption of the gas by the sample occurs; and a means for controlling the operation of the cooling means and the warming means responsive to the signal provided by the detector means.

The method disclosed for analyzing the surface area of a sample comprises: (a) providing the sample in a chamber; (b) contacting the sample with a gas capable of adsorbing onto the surface of the sample; (c) cooling the sample to a temperature at which the gas adsorbs onto the surface of the sample; (d) detecting the amount of gas adsorbed by the sample; (e) warming the sample to room temperature by directing a flow of room temperature air over the sample; (f) detecting the amount of gas desorbed by the sample; and (g) determining the surface area of the sample from the amounts of gas adsorbed and desorbed by the sample.

The present invention solves the deficiencies in the prior art by providing a means for rapidly and precisely bringing the temperature of the sample from liquid nitrogen to room temperature. This is accomplished preferably by means of a motor driven fan which directs a flow or room temperature air onto the sample chamber when the coolant container is lowered away from the sample chamber. The fan is activated by a signal from the detector indicating that adsorption of gas by the sample is complete.

By using the fan of the present invention, the time and manipulation steps required to run the procedure are reduced. Neither a second Dewar flask of water nor a heating mantle is required, and the operator does not have to change containers in the middle of the procedure. Since room temperature air is used, control over the temperature is maintained and the sample will not exceed room temperature. More accurate and reliable measurements, therefore, can be obtained.

Thus, it is a principal object of the present invention to provide an apparatus for cooling and warming a sample.

It is another object of the present invention to provide an apparatus for warming a cooled sample by directing a flow of room temperature air onto the cooled sample.

It is another object of the present invention to provide an apparatus for rapidly bringing a cooled sample to room temperature, without exceeding room temperature.

It is another object of the present invention to provide an automated apparatus for rapidly bringing a sample from liquid nitorgen temperature to room temperature.

It is another object of the present invention to provide an automated apparatus for rapidly bringing a sample from liquid nitrogen temperature to room temperature, which apparatus is activated in response to the cessation of adsorption or desorption of gas by the sample.

It is a further object of the present invention to provide an automated apparatus for performing a flowing gas surface area analysis on a sample with minimal user manipulation.

It is a further object of the present invention to provide an automated apparatus for determining the surface area of a sample by analyzing the amount of gas absorbed and desorbed by the sample at liquid nitrogen and at room temperatures, whereby the cooled sample is rapidly brought to room temperature.

Other objects, features, and advantages of the present invention will become apparent upon review of the following detailed description of embodiments of the invention, when taken in conjunction with the drawings. BRIEF DESCRIPTION OF THE DRAWING FIG. 1 is a perspective view of a sample warming and cooling apparatus embodying the present invention.

Figure 1:
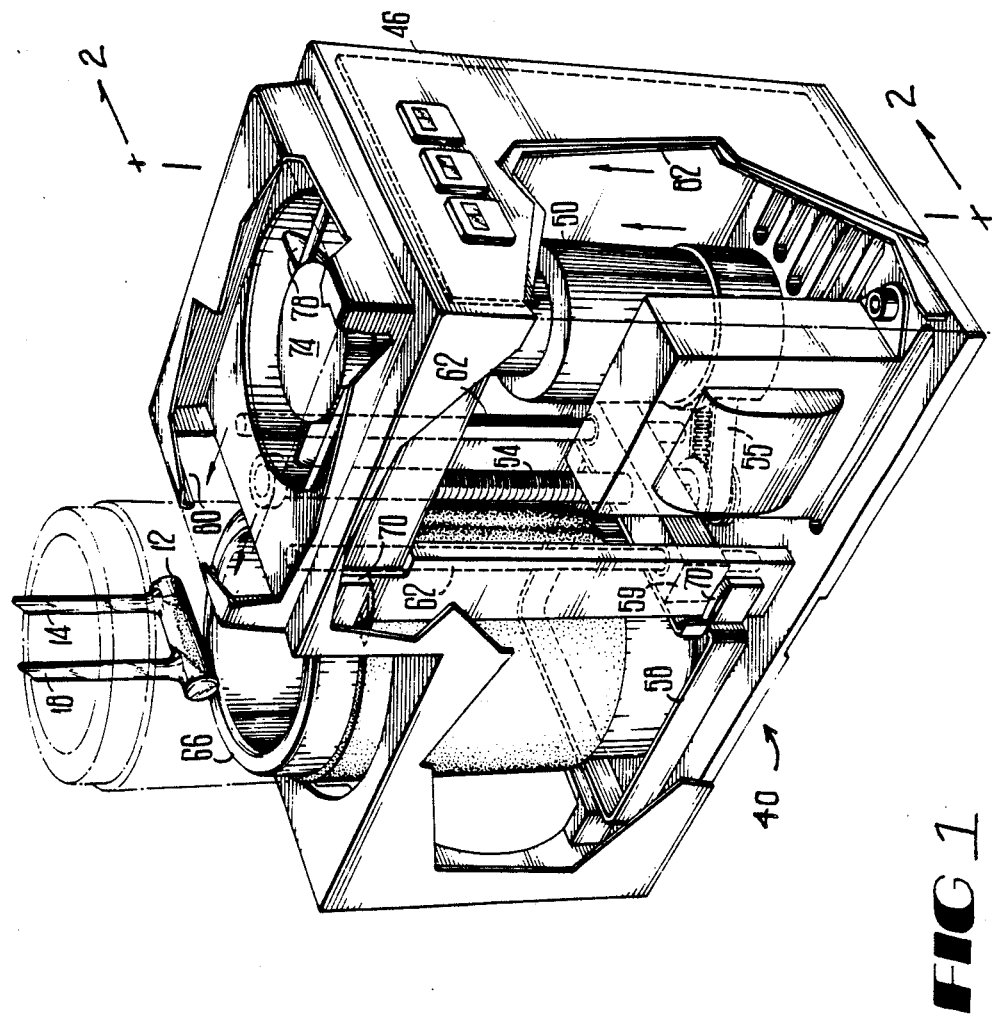
Figure 4:
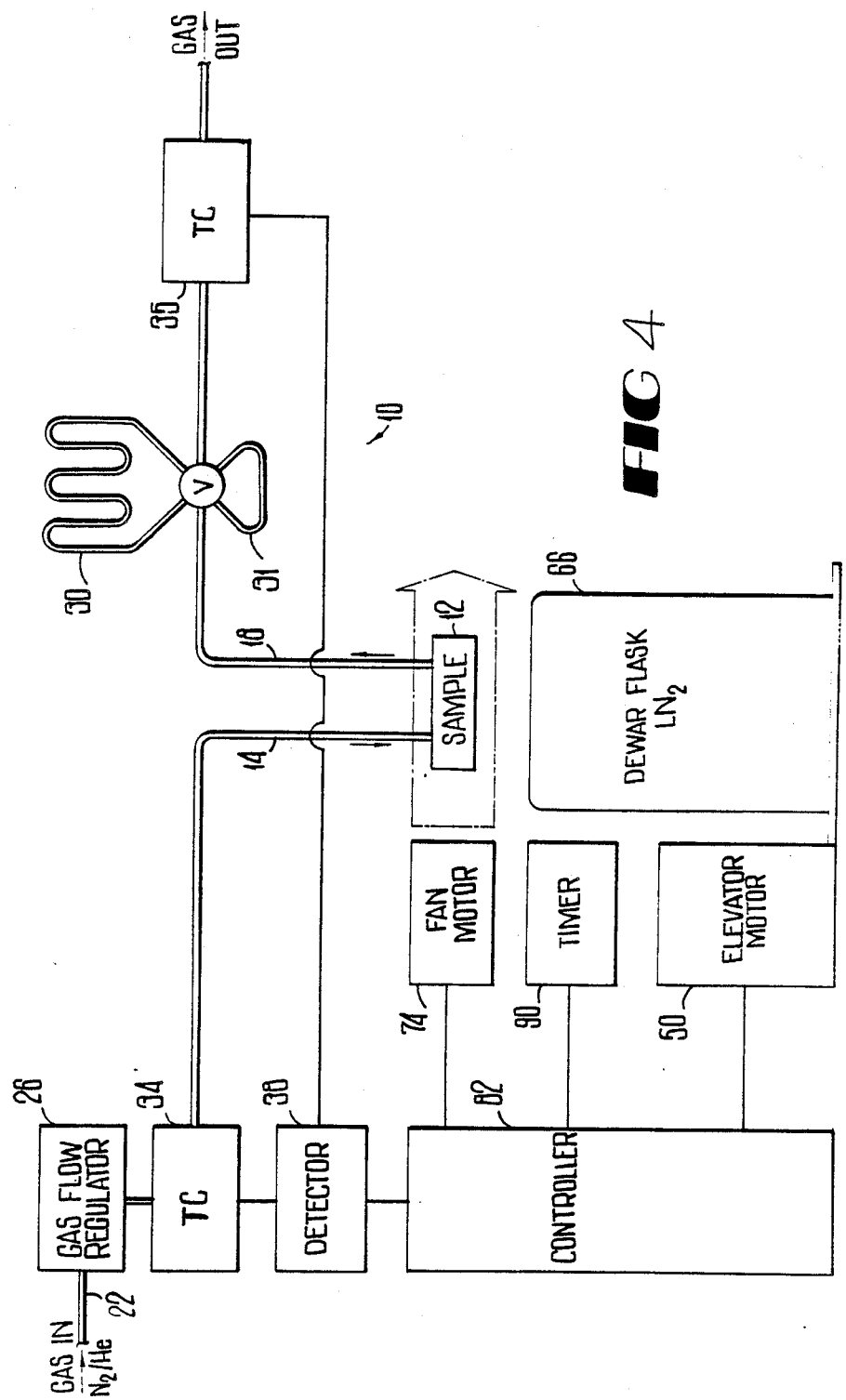

FIG. 4 is a block diagram illustrating the gas flow path and the analyzer with respect to the warming and cooling apparatus. DETAILED DESCRIPTION Referring now to the drawing, in which like numerals represent like parts throughout the several views, FIG. 1 shows a sample warming and cooling apparatus 40 having a housing, an elevator assembly for immersing the sample in a coolant contained in a Dewar flask, and a fan providing a vigorous directionalized flow of room temperature air onto the sample, which warms the sample up to room temperature, as will be described further hereinbelow.

Figure 2:
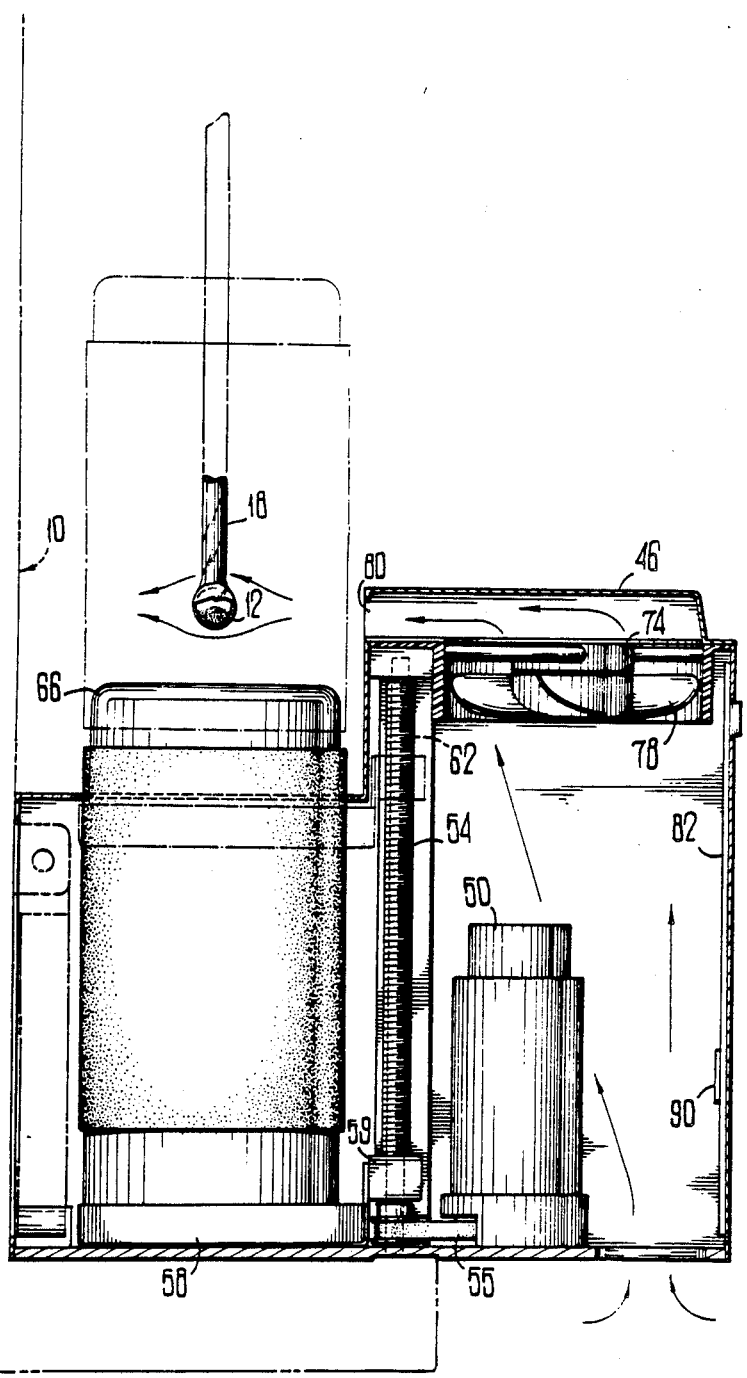
FIG. 2 is a side cutaway view of the device showing its relationship to the sample chamber and the analyzer, with portions broken away to show interior detail.

A sample chamber 12 is provided, which is charged with a solid material to be analyzed, preferably a powdered or granulated solid or porous material. Connected to the chamber 12 are a gas inlet tube 14 and a gas outlet tube 18 through which pass a gas mixture to be adsorbed onto the sample. As shown in FIG. 2, the inlet and outlet tubes are spaced outwardly from the analyzer cabinet and project downwardly to the sample chamber. The gas enters by way of a gas source 22 which is normally a gas tank or tanks. The choice of gases varies according to the requirements of the system, but is preferably a mixture of nitrogen ("$N_2$") and helium, ("He") representing an active and an inactive gas, respectively. A typical mixture composition is 30% $N_2$ and 70% He. A gas flow regulator 26 controls the mixture composition of the separate gases and the flow rate into the gas inlet tube 14.

Gas enters the sample chamber 12 and a portion of the gas is adsorbed by the sample when cooled and desorbed when the sample is subsequently warmed, as will be discussed in greater detail hereinbelow. Gas exits the chamber via the gas outlet tube 18 and can pass out into an appropriate recovery container.

The composition of the gas mixture is detected by means of a pair of thermal conductivity cells 34 and 35; a first cell 34 is positioned to monitor gas flow prior to the gas entering chamber 12, and a second cell 35 is positioned downstream to monitor gas after exiting from the chamber 12 via the gas outlet tube 18. The cells 34 and 35 are connected to the gas flow detector 38, which integrates the signal received from the thermal conductivity cells 34 and 35.

Two gas paths, labeled "short" and "long", are provided downstream from the sample chamber 12. The short path 31 can be used either during an analysis or calibration of the analyzer 10, when no extensive delay of gas flow is needed. A longer path is created by imposition of a delay path 30 consisting of an elongated tube or other means known by those skilled in the art for increasing the length of time for the gas to reach the second thermal conductivity cell 35. The purpose of the delay path will be discussed in greater detail hereinbelow. Briefly, however, it is designed to increase the distance the gas travels before reaching the cell 35 so that the temperature, pressure and flow rate of the gas stabilize prior to detection. The short path 31 is a tube directly connecting the gas outlet tube 18 with the cell 35. A user can switch between the long path and the short path using a switchable valve (not shown).

A surface area analyzer 10 equipped according to the invention includes a sample warming and cooling apparatus 40. The components of the apparatus 40 are contained, within a housing 46 adapted to be mounted to the analyzer 10 under the sample chamber 12 as shown in FIG. 2. The housing 46 has an opening 60 facing the analyzer, through which horizontally extends an elevator platform 58. The platform 58 is a flat generally rectangular tray which is fixedly connected to a mounting block 59. The mounting block 59 is threadably connected to a vertical threaded drive screw 54 which turns about its axis. A pair of guide rods 62 are mounted vertically and parallel to each other to the top and bottom of the housing near the opening 60. Each rod slidably passes through a bore in the mounting block 59 and assists in maintaining proper alignment of the platform 58 during operation. The screw 54 is located between the guides rods 62 in an orientation parallel to the rods 62 but is jounaled within a set of upper and lower bearings (not shown) mounted to the housing.

The screw 54 is operatively connected to an elevator motor 50 disposed within the housing 46 by means of a belt drive 55. Any other conventional engaging means such as a gear drive, can be used. Rotation of the drive screw causes the block 59, and thus the platform 58, to be raised or lowered along a vertical path.

A Dewar flask 66 rests on the platform 58 and contains the coolant used during the analysis procedure. This coolant is preferably liquid nitrogen, but can be any other suitable coolant, such as dry ice/acetone or the like. The configuration of the sample chamber 12, inlet tube 14 and outlet tube 18 allows the sample chamber 12 to be immersed in the coolant in the Dewar flask 66 when the flask is raised.

During operation the flask 66 is positioned directly under the sample chamber 12. When the elevator motor 50 is activated, the platform 58, carrying the flask 66, is raised by the turning of the screw 54 within the bore of the mounting block 59 so as to immerse the sample chamber 12 in the coolant. The raising or lowering is limited by a pair of limit switches 70 positioned at the raised and lowered positions of the platform. When the platform contacts the limit switch 70 at either end, a contact is made or broken which signals the elevator motor 50 to stop.

In a preferred embodiment, a fan motor 74, which operates a fan 78, is mounted within the housing 46 so that the airflow produced by the fan 78 is directed through an opening 80 in the housing 46. The fan is preferably mounted with a vertical axis of rotation so as to direct air upwardly into a small plenum 81 defined at the top of the housing 46. The opening 80 located on the vertical front panel of housing 46 facing the sample chamber 12 and preferably disposed above the opening 60 in order to be in a generally direct line with the sample chamber 12. The opening 80 channels, or directs, air passing from the fan 78 onto the sample chamber 12, as shown by the arrows in FIG. 2.

Air passing through the fan 78 comes from the surrounding environment within and outside of the housing 46, and is thus at room temperature. Air from the fan 78 contacting the sample chamber 12 is also at room temperature.

The air path defined by the opening 80 may be partially blocked by the Dewar flask 66 when the platform 58 is in a raised position, but the opening 80 is unobstructed when the platform 58 is in a lowered position. Therefore, when the coolant is removed from around the sample chamber 12, the opening 80 is in direct proximity to the sample chamber 12 to channel the room temperature air flow from fan 78 to warm the sample chamber 12.

The operation of the mechanical elements is controlled by a controller 82, which properly sequences the mechanical steps of the analysis and reduces operator involvement. The controller 82 contains a Programmed Logic Array ("PLA") and a timer 90. The PLA monitors and processes the signals transmitted by the detector 38 when gas is adsorbed or desorbed. The controller 82 activates elevator motor 50 to raise or lower the platform 58 and activates or deactivates the fan motor 74. The time 90 communicates with the PLA and regulates the timing of when the elevator motor 50 and the fan motor 74 are activated or deactivated. Both the controller 82 and the timer 90 are preferably resident within the housing 46. The controller 82 can be programmed to carry out functions described below by a programmer of ordinary skill.

The delay path 30 comprises a long tube that increases the distance that the gas must travel between the sample chamber 12 and the thermal conductivity cell 35. The delay path 30 is used when testing for pore volume or testing materials of relatively high surface area, which may desorb too much gas over too long a time for easy accurate measurement. Delaying the gas allows the flow rate to return to normal without overloading the cell 35. The stabilized flow rate is more comparable to the flow rate of hte reference measurements, and therefore, when the analyzer 10 integrates the change in concentration, a correct basis of comparison is made between the reference measurements and the sample analysis. Only a short time elapes before the gas traverses the delay path 30. Therefore, the temperature of the sample must be raised quickly so that desorption occurs rapidly and the equilibrium blow rate can be regained before the gas reaches the cell 35.

Figure 3:
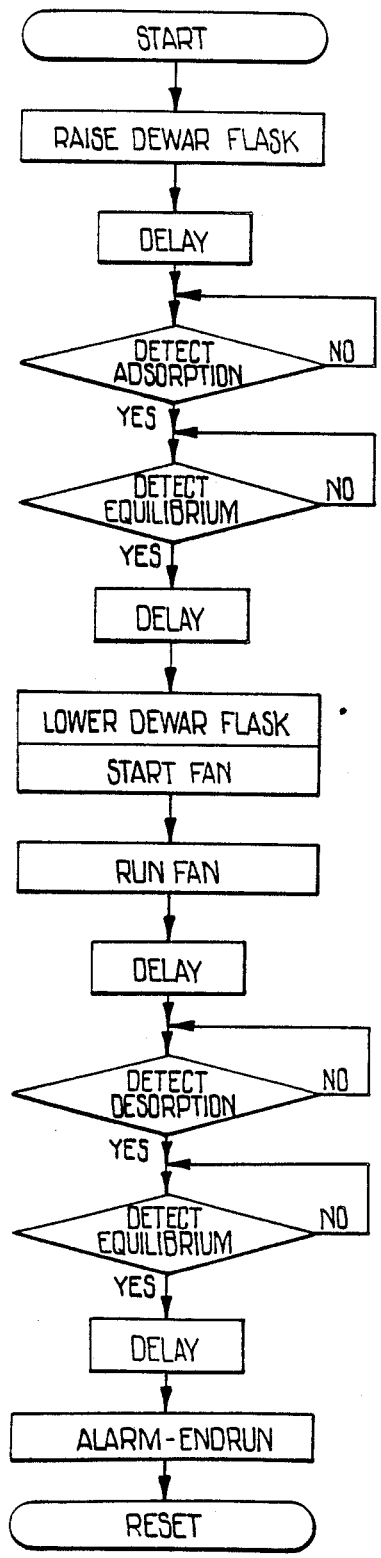
FIG. 3 is a flow diagram illustrating the analysis process.

The operation of the sample warming and cooling apparatus 40 will now be described with reference to the flow diagram of FIG. 3. In performance of a sample analysis, first the sample is poured into the sample chamber 12. The sample is initially heated with the mixed gas flowing about it it drive off gas and vapors picked up during exposure to the atmosphere, and then cooled to room temperature and positioned for analysis. The mixed gas flow is continued, but the sample temperature must be reduced to the temperature of liquid nitrogen to bring about adequate adsorption of nitorgen gas from the gas stream. This is preferably accomplished by arranging the sample in the chamber 12 with the inle tube 14 and the outlet tube 18 extending vertically so that the Dewar flask 66 of liquid nitrogen can be brought upward by raising the platform 58 to immerse the sample and the lower portions of the tubes 14 and 18. The thermal conductivity cell 34 detects the gas flow prior to the gas mixture entering the sample chamber 12, as shown in FIG. 4. The quantity of $N_2$ measured will be used as a reference comparison level when the gas is detected after exiting the sample chamber 12.

The operator initiates the mechanical analysis sequence by activating a start switch (not shown) on the controller 82. This activates the elevator motor 50 to raise the platform 58 and flask 66 until limit switch 70 is contacted. The timer 90 is then activated and starts a delay period, which is preferably about one minute. This period allows for complete cooling of the sample and assures that adsorption is occurring.

In the analyzer 10, the detector 38 measures the change in thermal conductivity of the gas mixture in the outlet tube 18 as $N_2$ is adsorbed by the cooled sample. As $N_2$ is adsorbed a peak will be reached when adsorption is at its maximum; then the level will return to an equilibrium baseline. The PLA compares the detector signal to the stored starting concentration of $N_2$. When the baseline is again detected, the timer 90 is set for a further delay of from about 30 seconds to one minute, although the time can vary without substantial detrimental effect.

At the end of the delay the timer 90 signals the PLA, which activates the elevator motor 50 to lower the platform 58. As the Dewar flask 66 is lowered from the sample chamber 12, the the PLA also activates the fan motor 74. Room temperature air is drawn through the fan 78 and is directed by the opening 80 in a vigorous stream onto the sample chamber 12 for a period of time, preferably about one minute. It is important to bring the sample up to room temperature as rapidly as possible, yet without exceeding room temperature. Room temperature should not appreciably be exceeded because the analyzer is calibrated at room temperature and pressure. Comparable conditions will provide the greatest accuracy and reproducibility of measurements. The apparatus 40 cannot raise the sample temperature above room temperature because the heating fluid is at room temperature.

The detector 38 monitors the cell 35 and measures the desorption of $N_2$ from the surface of the sample. A desorption peak will occur as $N_2$ is released from the surface of the sample followed by a return to an equilibrium baseline after all the $N_2$ is released. The controller 82 will continue the delay until the detector 38 measures the establishment of the equilibrium baseline and, after a further delay of about 30 seconds to one minute to allow for complete desorption, an alarm signal is generated, alerting the operator of the end of the run. The controller 82 and the timer 90 are then reset for the next run of the analyzer.

In an altenrative embodiment an air tube connected to a pump or other positive pressure means can be used to provide a stream of room temperature air directed onto the sample chamber.

The present invention can also be used in such applications as in a chemistry laboratory reaction apparatus where a reaction mixture must be cooled in order for reaction to occur and then rapidly warmed to room temperature to quench reaction. Other variations are contemplated by the invention.

While this invention has been described in detail with particular reference to preferred embodiments thereof, it will be understood that variations and modifications can be effected within the spirit and scope of the invention as described herein before and as defined in the appended claims.

What is claimed is:

1. A flowing gas surface area analyzer, comprising:
   a sample chamber for containing a sample of material to be analyzed;
   means for flowing a stream of gas through said sample chamber containing said sample;
   detector means for receiving said stream of gas downstream from said sample chamber and for providing a signal correlative with adsorption or desorption of said gas by said sample;
   means for cooling said sample to a temperature at which adsorption of said gas by said sample occurs;
   means for warming said sample comprising means for directing a flow of room temperature air over said sample chamber such that said sample is warmed to a temperature at which desorption of said gas by said sample occurs; and
   means for controlling the operation of said cooling means and said warming means responsive to said signal provided by said detector means.

2. The analyzer of claim 1, wherein said warming means comprises a motor driven fan which directs a flow of room temperature air onto said chamber.

3. The analyzer of claim 2, wherein said fan is activated when adsorption of said gas is complete and said cooling means is removed from said sample.

4. The analyzer of claim 1, wherein said gas comprises a mixture of gases.

5. The analyzer of claim 4, wherein said gas comprises a mixture of nitrogen and helium.

6. The analyzer of claim 1, wherein said cooling means comprises a container containing a coolant such that when immersed said sample is cooled to a temperature at which adsorption of said gas by said sample occurs.

7. The analyzer of claim 6, wherein said coolant is liquid nitrogen.

8. A method for analyzing the surface area of a sample, comprising:
   (a) providing said sample in a chamber;

(b) contacting said sample with a gas capable of adsorbing onto the surface of said sample;
(c) cooling said sample to a temperature at which said gas adsorbs onto the surface of said sample;
(d) detecting the amount of gas adsorbed by said sample;
(e) warming said sample to room temperature by directing a flow of room temperature air over said sample;
(f) detecting the amount of gas desorbed by said sample; and
(g) determining the surface area of said sample from the amounts of gas adsorbed and desorbed by said sample.

9. An apparatus for analyzing the surface area of a sample, comprising:
(a) means defining a chamber for holding said sample;
(b) means for contacting said sample with a gas capable of adsorbing onto the surface of said sample;
(c) means for cooling said sample to a temperature at which said gas adsorbs onto the surface of said sample;
(d) means for warming said sample to a temperature at which said gas desorbs from the surface of said sample by directing a flow of room temperature air over said sample; and
(e) means for detecting the amount of gas adsorbed or desorbed by said sample.

10. The apparatus of claim 9 wherein said cooling means comprises a coolant chamber containing a coolant in which said sample is immersed.

11. The apparatus of claim 10 further comprising operation controlling means associated with said cooling means for raising or lowering said cooling means between a first lower position and a second upper position whereby said chamber is at least partially immersed in said coolant when said container is raised in said second upper position.

12. The apparatus of claim 11, wherein said coolant is liquid nitrogen.

13. A method for analyzing the surface area of a sample, comprising:
(a) providing said sample in a chamber;
(b) contacting said sample with a gas capable of adsorbing onto the surface of said sample;
(c) cooling said sample to a temperature at which said gas adsorbs onto the surface of said sample;
(d) detecting the amount of gas adsorbed by said sample;
(e) warming said sample to room temperature by directing a flow of room temperature fluid over said sample;
(f) detecting the amount of gas desorbed by said sample; and
(g) determining the surface area of said sample from the amounts of gas adsorbed and desorbed by said sample.

14. The method of claim 13, wherein said fluid is gaseous.

15. An apparatus for analyzing the surface area of a sample, comprising:
(a) means defining a chamber for holding said sample;
(b) means for contacting said sample with a gas capable of adsorbing onto the surface of said sample;
(c) means for cooling said sample to a temperature at which said gas adsorbs onto the surface of said sample;
(d) means for warming said sample to a temperature at which said gas desorbs from the surface of said sample by directing a flow of room temperature fluid over said sample; and
(e) means for detecting the amount of gas adsorbed or desorbed by said sample.

16. The apparatus of claim 15 wherein said fluid is gaseous.

* * * * *